US007101553B2

(12) United States Patent
Haschke et al.

(10) Patent No.: US 7,101,553 B2

(45) Date of Patent: Sep. 5, 2006

(54) IMMUNE RESPONSE ENHANCEMENT METHODS

(75) Inventors: Ferdinand Haschke, Frankfurt a/Main (DE); Anne-Lise Carrie, Unteriberg (CH); Zdenek Kratky, New Milford, CT (US); Harriet Link-Amster, Vevey (CH); Florence Rochat, Montreux (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 10/822,799

(22) Filed: Apr. 13, 2004

(65) Prior Publication Data

US 2004/0191234 A1 Sep. 30, 2004

Related U.S. Application Data

(60) Division of application No. 10/228,722, filed on Aug. 26, 2002, now abandoned, which is a continuation of application No. PCT/EP01/01627, filed on Feb. 14, 2001.

(30) Foreign Application Priority Data

Mar. 1, 2000 (EP) ................................. 00200735

(51) Int. Cl.
*A61K 39/165* (2006.01)
*A61K 39/20* (2006.01)

(52) U.S. Cl. .............................. 424/184.1; 424/212.1; 424/219.1

(58) Field of Classification Search ............. 424/184.1, 424/212.1, 219.1; 514/896
See application file for complete search history.

(56) References Cited

U.S. PATENT DOCUMENTS

| | | | |
|---|---|---|---|
| 4,954,622 A | 9/1990 | Cooper | 536/127 |
| 5,051,408 A | 9/1991 | Cooper | 514/54 |
| 5,422,346 A | 6/1995 | Mitchell et al. | 514/54 |
| 5,721,345 A | 2/1998 | Roberfroid et al. | 536/4.1 |
| 5,895,648 A * | 4/1999 | Cavaliere Vesely et al. | 424/93.4 |
| 6,203,797 B1 | 3/2001 | Perry | 424/195.1 |

FOREIGN PATENT DOCUMENTS

| | | |
|---|---|---|
| EP | 0692252 A1 | 1/1996 |
| WO | WO 87/02679 | 5/1987 |

OTHER PUBLICATIONS

Firmansyah, A. et al ("Improved Humoral Immune Response To Measles Vaccine In Infants Receiving Infant Cereal With Fructooligosaccharides", Journal of Pediatric Gastroenterology and Nutrition, 2000; 31).*

Agostoni, C. et al (Prebiotic Oligosaccharides in Dietetic Products for Infants: A Commentary by the ESPGHAN Committee on Nutrition, 2004;39: 465-473).*

Roberfroid, M. (Prebiotics and probiotics: are they functional foods?, Am J Clin Nutr, 2000;71: 1682s-7s).*

Dictionary definitions for stimulate, enhance and consumed.*

Collins et al., XP-00972408, "Probiotics, prebiotics and synbiotics: approaches for modulating the microbial ecology of the gut," *Am. J. Clin. Nutr.*, vol. 69, No. Suppl. pp. 1052S-1057S (1999).

Firmansyah et al., XP-001000242, "Improved Humoral Response to Measles Vaccine in Infants Receiving Infant Cereal With Fructooligosaccharides," *Journal of Pediatric Gastroenterology and Nutrition*, vol. 31, No. Suppl. 12 (2000).

Ziemer et al., XP-000972201, "An Overview of Probiotics, Prebiotics and Synbiotics in the Functional Food Concept: Perspectives And Future Strategies," *International Dairy Journal*, vol. 8, pp. 473-479 (1998).

* cited by examiner

*Primary Examiner*—Lynette R. F. Smith
*Assistant Examiner*—Lakia J. Tongue
(74) *Attorney, Agent, or Firm*—Bell, Boyd & Lloyd LLC

(57) ABSTRACT

A prebiotic for enhancement of an immune response, a nutritional composition for enhancement of an immune response; use of a prebiotic in the manufacture of a medicament or nutritional composition for enhancement of an immune response; use of a prebiotic in the manufacture of a medicament or nutritional composition for the prevention or treatment of measles; a method of enhancing an immune response which comprises administering an effective amount of a prebiotic; and a method of prevention or treatment of measles which comprises administering an effective amount of a prebiotic. In preferred embodiments the prebiotic comprises a fructo-oligosaccharide.

13 Claims, No Drawings

IMMUNE RESPONSE ENHANCEMENT METHODS

CROSS-REFERENCE TO RELATED APPLICATIONS

This application is a divisional of U.S. application Ser. No. 10/228,722, filed Aug. 26, 2002, now abandoned, which is a continuation of the U.S. national stage designation of International application PCT/EP01/01627, filed Feb. 14, 2001, the entire contents of each of which are expressly incorporated herein by reference thereto.

BACKGROUND ART

The present invention relates to a carbohydrate formulation for enhancement of an immune response, a nutritional composition for enhancement of an immune response; and to the use of a prebiotic formulation in the manufacture of a medicament or nutritional composition for enhancement or improvement of an immune response to a vaccination, in particular measles vaccination, and prevention and supportive treatment of diseases and infections e.g. bacterial, viral and parasitic. The invention also relates to a method of enhancing an immune response which comprises administering an effective amount of a prebiotic mixture; and a method of prevention or supportive treatment of diseases which comprises administering an effective amount of a prebiotic formulation.

It is well known that prebiotics comprise carbohydrates and more specifically, oligosaccharides. Furthermore it is known that they have widely been used as functional food ingredients. They resist hydrolysis by enzymes of the human digestive tract, can reach the colon undegraded and provide a carbohydrate substance particularly suited to the growth of bifidobacteria. Oligosachharides may be produced from glucose, galactose, xylose, maltose, sucrose, lactose, starch, xylan, hemicellulose, inulin, or a mixture thereof. Purified commercially available products such as fructo-oligosaccharides contain greater than about 95% solids in the form of oligosaccharides.

Measles is a major public health problem, infecting approximately 70 million children annually, and it is estimated that 2 million die each year from the disease itself or its complications. In addition to fever and rash, the consequences of measles include acute diarrhea or dysentery, pneumonia, encephalitis, and blindness due to acute vitamin A deficiency. Thus in developing countries, case fatality rates may reach 10–20% (Semba R. D. Clin. Infect. Dis. 1994; 19:489–499).

Measles prevention is possible by maintaining a high level of immunization through vaccination with attenuated live vaccine. Measles vaccine is usually given at 15 months but may be given earlier (at 6–9 months of age) in areas where disease is frequently occurring and poses a threat to health and life of children. However, the response to measles vaccination at less than 12 months of age is suboptimal because infants may transplacentally acquire maternal antibodies that disappear at a variable rate. Because the seroconversion rate following immunization is not 100% and there may be some waning of immunity with time, a second immunization against measles is usually indicated.

An elevated response to early measles vaccination may therefore offer substantial and longer lasting protection until a second vaccine is administered, and the present invention provides a solution that addresses the problems set out above.

SUMMARY OF THE INVENTION

Remarkably, it has now been found that children fed a diet comprising a prebiotic formulation have a significantly enhanced immune response after vaccination than children fed a control diet without this prebiotic formulation.

Consequently, in a first aspect, the present invention provides a composition comprising at least one prebiotic for enhancement of an immune response.

In a second aspect, the invention provides use of a prebiotic in the manufacture of a medicament or nutritional composition for enhancement of an immune response.

In a third aspect, the invention provides use of a prebiotic or composition in the manufacture of a medicament or nutritional composition for the prevention or supportive treatment of measles.

In a fourth aspect, the invention provides a method of enhancing an immune response which comprises administering an effective amount of a prebiotic or composition comprising at least one prebiotic.

In a fifth aspect, the invention provides a method of prevention or supportive treatment of diseases such as measles which comprises administering an effective amount of a prebiotic or composition comprising at least one prebiotic.

Advantageously, an embodiment of the composition is a nutritional composition which comprises at least one prebiotic. Preferably, the prebiotic comprises an oligosachharide produced from glucose, galactose, xylose, maltose, sucrose, lactose, starch, xylan, hemicellulose, inulin, or a mixture thereof. More preferably, the oligosaccharide comprises fructo-oligosaccharide. Most preferably, the prebiotic is a mixture of fructo-oligosaccharide and inulin sold under the trademark PREBIO1® or a mixture of oligofructose sold under the trademark RAFTILOSE® and inulin sold under the trademark RAFTILINE®.

The prebiotic advantageously comprises about 50% to about 90% fructo-oligosaccharide. More preferably, it comprises about 60% to about 80% fructo-oligosaccharide. Most preferably, it comprises about 70% fructo-oligosaccharide.

Preferably, the prebiotic comprises about 10% to about 50% inulin. More preferably, it comprises about 20% to about 40% inulin. Most preferably, it comprises about 30% inulin.

The composition may include a probiotic in addition to the prebiotic. Preferably, the probiotic is selected from the group consisting of *Bifidobacterium bifidum* and *streptococcus thermophilus*. Preferably the *Bifidobacterium bifidum* is *Bifidobacterium lactis*.

DETAILED DESCRIPTION OF THE PREFERRED EMBODIMENTS

An advantage of the present invention is that it provides an elevated immune response after vaccination and therefore offers substantial protection until a second follow-up vaccine can be administered.

Another advantage of the present invention is that it provides an elevated response to early measles vaccination may therefore offer substantial protection against measles until a second measles vaccine is administered.

Yet another advantage of the present invention is that it may be employed to enhance an immune response, e.g., protection against measles, by simple consumption of food before, during, and after the vaccination period. It will be appreciated that intravenous or subcutaneous administration of a drug requires expertise, and compared to oral administration it is not as safe, convenient or acceptable to the patient. In the light of these concerns, the invention provides the clear advantage of a nutritional and/or therapeutic product which may be administered orally although other forms of administration can be used.

Additional features and advantages of the present invention are described in, and will be apparent from, the following description of the presently preferred embodiments.

In an embodiment, a nutritional composition comprises a milk based cereal together with a prebiotic formulation. Preferably the milk based cereal is an infant cereal which acts as a carrier for the prebiotic formulation.

The most preferred prebiotic comprises a mixture of fructo-oligosaccharides and inulin in the amounts by weight of 70% fructo-oligosaccharides and 30% inulin.

If desired and advantageously, the composition may include a source of protein and/or a source of carbohydrate and/or a source of fat.

Dietary protein is preferred as a source of protein. The dietary protein may be any suitable dietary protein; for example animal protein, such as milk protein, meat protein or egg protein; vegetable protein, such as soy protein, wheat protein, rice protein, and pea protein; a mixture of free amino acids; or a combination thereof. Milk proteins such as casein, whey proteins or soy protein or a mixture thereof are particularly preferred.

The composition may comprise a fat source, and if so the fat source preferably provides about 5% to about 55% of the energy of the composition; for example about 20% to about 50% of the energy. Lipid making up the fat source may be any suitable fat or fat mixture. For example soy oil, palm oil, coconut oil, safflower oil, sunflower oil, corn oil, canola oil, lecithins or animal fat such as milk fat may be added if desired.

A source of carbohydrate may also be included. If so, it preferably provides about 40% to about 80% of the energy of the composition. Any suitable carbohydrate may be used, for example sucrose, lactose, glucose, fructose, corn syrup solids, maltodextrin, or a mixture thereof.

Also, dietary fibers can be included, if desired. When present, it comprises up to about 5% of the weight of the nutritional composition. The dietary fibers may be provided from any suitable origin, including for example soy, pea, oat, pectin, guar gum, gum arabic, fructo-oligosaccharide or a mixture thereof.

Suitable vitamins and minerals may be included in the nutritional composition in an amount to meet the appropriate or desirable guidelines.

One or more food grade emulsifiers may be included in the nutritional composition if desired; for example diacetyl tartaric acid esters of mono- and di-glycerides, lecithin and mono- or di-glycerides or a mixture thereof. Similarly suitable salts and/or stabilizers may be included.

The nutritional composition for enhancing an immune response e.g., following measles, vaccination is preferably enterally administrable; for example in the form of a powder, tablet, capsule, a liquid concentrate, solid product or a ready-to-drink beverage. If it is desired to produce a powdered nutritional formula, the homogenized mixture is transferred to a suitable drying apparatus such as a spray drier or freeze drier and converted to powder.

Alternatively, a usual food product may be enriched with the an embodiment of composition. For example, a fermented milk, a yogurt, a fresh cheese, a renneted milk, a confectionery bar, breakfast cereal flakes or bars, a drink, milk powder, soy-based product, non-milk fermented product or a nutritional supplement for clinical nutrition. Then, the amount of the composition added is preferably at least about 0.01% by weight.

An embodiment of the composition may be included in article of confectionery, for example a sweet or sweetened beverage.

EXAMPLES

The following examples are given by way of illustration only and in no way should be construed as limiting the subject matter of the present application. Percentages and parts are by weight unless otherwise indicated.

Example 1

Nutritional Composition

A composition was made by blending a cereal product with 4% prebiotic (70% fructo-oligosaccharide, 30% inulin). Its composition is indicated below:

| component | amount in % |
|---|---|
| Cereal product | 96% |
| Prebiotic | 4% |

Infants received 1–2 servings of this composition or cereal without the prebiotic (per serving 25 g cereal and 70 ml of water) per day throughout a 10 week study period. The amount of cereal consumed per day was recorded. No restrictions were made for intake of milk, solids or family food.

Remarkably, if a nutritional composition according to the invention was consumed it was found that the concentration of IgG antibody 10 weeks after a measles vaccination was significantly higher compared to consumption of a similar nutritional composition without the prebiotics. Remarkably the concentration of IgG antibodies in the blood has been found to be significantly increased when the composition comprising prebiotics was consumed. Surprisingly the level of IgG was at least 50% higher.

A double-blind randomized controlled study was conducted to examine the effects on the immune response after measles vaccination of an infant cereal with milk (Nestle) supplemented with a “prebiotic” mixture of fructo-oligosaccharides and inulin (PREBIO1®).

Eight months-old infants with mixed feeding (breast-, formula, and solids) were randomly assigned to two groups. Both groups received the cereals during a period of 10 weeks, and one group was supplemented with the PREBIO1® mixture of fructo-oligosaccharides and inulin (Ig per 25 g cereal). Four weeks after introduction of the cereals, all infants were vaccinated with live attenuated measles vaccine (Biofarma, Indonesia). Blood was collected for IgG measles antibody measurement (Elisa; PanBio, Australia) immediately before and 6 weeks after vaccination. Growth, general health status and mild reactions after vaccination (e.g. fever, runny nose) were recorded.

Out of 50 infants enrolled, 24 infants having their diets supplemented with a composition according to the invention (S) and 25 controls not having their diets supplemented with a composition according to the invention (C) completed the study. Post-vaccination IgG antibody levels were significantly higher ($p<0.05$) in group S.

IgG antibodies increased 6.6 and 4.2 fold in groups S and C respectively ($p<0.03$). The post-vaccination IgG positivity rates were 96% (S) and 88% (C). Mild reactions were significantly more often observed in group S ($p<0.01$). No differences in growth and overall health status were observed.

It was concluded that regular consumption of infant cereals with the prebiotic composition according to the invention improved immune response e.g., after measles vaccination.

Example 2

Food Supplement

A food supplement was prepared by mixing or blending fructo-oligosaccharide with inulin in the proportions by weight of about 70% fructo-oligosaccharide to about 30% inulin. The resulting prebiotic mixture may be added or blended with any suitable carrier, for example a fermented milk, a yogurt, a fresh cheese, a renneted milk, a confectionery bar, breakfast cereal flakes or bars, a drink, milk powder, soy-based product, non-milk fermented product or a nutritional supplement for clinical nutrition.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A method of enhancing an immune response to measles after a measles vaccine which comprises administering at least one prebiotic or nutritional composition comprising at least one prebiotic to an individual that has received the measles vaccine, where in the prebiotic is present in an amount sufficient to enhance an immune response to measles after a measles vaccine.

2. The method of claim 1, wherein the at least one prebiotic or nutritional composition comprising at least one prebiotic is administered to a subject, wherein the prebiotic is present in an amount sufficient to enhance a measles immune response.

3. The method of claim 1, wherein the prebiotic comprises an oligosaccharide produced from glucose, galactose, xylose, maltose, sucrose, lactose, starch, xylan, hemicellulose, inulin, or a mixture thereof.

4. The method of claim 1, wherein the prebiotic comprises a fructo-oligosaccharide.

5. The method of claim 1, wherein the prebiotic comprises a mixture of fructo-oligosaccharide and inulin.

6. The method of claim 1, wherein the prebiotic comprises, by weight, about 60% to about 80% fructo-oligosaccharide and about 20% to about 40% inulin.

7. The method of claim 1, wherein the prebiotic or nutritional composition further comprises a probiotic.

8. The method of claim 7, wherein the prebiotic is selected from the group which consists of *Bifidobacterium bifidum* and *Streptococcus thermophilus*.

9. The method of claim 1, wherein the at least one prebiotic or nutritional composition is administered in combination with a carrier.

10. The method of claim 9, wherein the carrier comprises a source of protein, a source of carbohydrate, a source of fat, or a combination thereof.

11. The method of claim 9, wherein the carrier comprises cereal, fermented milk, yogurt, cheese, renneted milk, confectionery bar, beverage, milk powder, soy-based product, non-milk fermented product, or clinical nutrition supplement, or a combination thereof.

12. The method of claim 11, wherein the carrier comprises infant cereal a source of protein and/or a source of carbohydrate and/or a source of fat.

13. A method for preventing measles and enhancing an immune response to measles which comprises:

administering a measles vaccine to a subject; and administering at least one prebiotic or nutritional composition comprising at least one prebiotic to the subject, wherein the prebiotic is present in an amount sufficient to enhance a measles immune response.

* * * * *